United States Patent [19]
Likibi

[11] Patent Number: 5,919,990
[45] Date of Patent: Jul. 6, 1999

[54] RECLAMATION OF BISPHENOL TARS AS FEEDSTOCK IN THE SYNTHESIS OF AMINOPHENYLHYDROXPHENYLALKANES

[75] Inventor: Parfait J.M. Likibi, Newburgh, Ind.

[73] Assignee: General Electric Company, Pittsfield, Mass.

[21] Appl. No.: 08/954,505

[22] Filed: Oct. 20, 1997

Related U.S. Application Data

[63] Continuation-in-part of application No. 08/732,109, Oct. 15, 1996, abandoned.
[51] Int. Cl.$^6$ ................................................ C07C 39/16
[52] U.S. Cl. ........................... 568/724; 564/425; 564/438
[58] Field of Search .................................... 564/438, 425, 564/724

[56] References Cited

U.S. PATENT DOCUMENTS 4,327,229  4/1982  Mendiratta .

*Primary Examiner*—Brian M. Burn

[57] ABSTRACT

The disclosure is of a process for recovering valuable by-products of the condensation of phenol and a ketone from a mother liquor obtained for example upon crystallization of a 1:1 adduct of phenol and bisphenol, said mother liquor containing phenol, bisphenol, isomers, contaminant by-products of the condensation reaction of phenol with the ketone and acidic impurities. The mother liquor is distilled/evaporated leaving a tarry residue, which is the feedstock for the process of the invention. The recovery comprises heating the feedstock with proportions of an arylamine salt, to extract the bisphenol-A values as aminophenylhydroxylphenyl-alkanes.

6 Claims, No Drawings

RECLAMATION OF BISPHENOL TARS AS FEEDSTOCK IN THE SYNTHESIS OF AMINOPHENYLHYDROXPHENYLALKANES

CROSS-REFERENCE TO RELATED APPLICATIONS

This is a continuation-in-part of application Ser. No. 08/732,109 filed Oct. 15, 1996, abandoned.

BACKGROUND OF THE INVENTION

1. Field of the Invention

The invention relates to synthesis of aromatic amines and more particularly to the synthesis of aminophenylhydroxyphenylalkanes.

2. Brief Description of Related Art

The aminophenylhydroxyphenylalkanes are a well known class of compounds useful as precursors for ultra-violet light absorbing agents in plastic formulations. The compounds, hereinafter referred to at times as "AHA's" may be prepared by a number of known methods. There are two main routes for the synthesis of AHA: the first one involves the reaction of aniline hydrochloride or related salts with p-isopropenyl phenol; see for example the descriptions given in German Auslegeschrift 1,251,334 and German Offenlegungsschrift 2,945,179. The second main route of synthesis involves the reaction of aniline hydrochloride with the dihydric phenol 2,2 bis(p-hydroxyphenyl) propane (commonly referred to as "bisphenol-A"); see for example the descriptions given in French Patent 1,398,652 and in Belgian Patent No. 633,236. Patent No. 633,236.

Bisphenols are commercially prepared by condensing 2 moles of phenol with a mole of ketone in the presence of an acid catalyst. The phenol is present in a molar excess of the stoichiometric requirement. During the condensation, a number of isomeric forms of the product bisphenol are formed which are contaminants of the desired bisphenol. These contaminants are carried in the product stream from the condensation reaction zone, with water, trace quantities of acidic materials derived from the catalyst, unreacted phenol and unreacted ketone. Currently, the purification of the desired product bisphenol is a costly and multi-step procedure.

There are two commercially important processes for the synthesis of bisphenols currently in use. The earlier process is called the "hcl" process, in reference to the acidic catalyst employed (hydrogen chloride). Briefly, glass lined vessels are charged in a batch/continuous fashion, with phenol, ketone and recycled by-products from earlier synthesis. This mixture is continually kept under a positive pressure of hydrogen chloride gas (hcl), which catalyzes the formation of bisphenol.

The second commercial synthesis reaction consists of passing phenol, acetone and the recycled by-products through a stationary bed of acidic ion exchange resin (IER) catalyst. This can be done in one of two ways; first, until essentially complete acetone depletion; second, and most desirable, is "partial acetone conversion". This technology is described in U.S. Pat. No. 5,315,042 which is hereby incorporated herein by reference thereto.

Representative of more detailed descriptions of the above commercial processes for condensing phenol with acetone to obtain bisphenol-A are those found in the U.S. Pat. Nos. 4,346,247; 4,396,728; 4,400,555; 4,424,283; 4,584,416; 4,766,254 and 4,847,433; all of which are incorporated herein by reference thereto. The factor shared by all of these known methods and processes is the need to purify and recover the product bisphenol in steps subsequent to the condensation reaction. Another shared factor is described in the U.S. Pat. No. 4,327,229 (incorporated by reference) which concerns the recovery of valuable products and by-products of bisphenol-A synthesis. In U.S. Pat. No. 4,327,229 recognition is given to a problem concerning the preparative reaction effluent, which contains unreacted phenol, unreacted acetone, acid residues of the catalyst, water, tars and by-product isomers of bisphenol-A in admixture with the desired bisphenol-A;

As mentioned above, all of the commercial processes to prepare bisphenol include costly multi-step purification procedures entailing distillations, crystallizations, solvent extractions, evaporations and like procedures. Where bisphenol is separated from the contaminants and purified by crystallization, a mother liquor is obtained which contains (after dewatering) lower boiling reaction by-products, bisphenol and higher boiling reaction by-products to name a few components. A part of this mother liquor is conventionally recycled to the condensation reactor for utilization in the preparative process, but a large part is purged from the process line to maintain the quality of the desired bisphenol and to avoid build-up of the undesirable by-products in the process line. The purged mother liquor may be subjected to further treatment to extract solvents, bisphenol, water and other useful components, but there ultimately results a residual tar which is generally burned as a means of disposal. However, as stated in the U.S. Pat. No. 4,327,229, "it has been calculated that substantial amounts of phenol and re-usable bisphenol-A values can be derived from the tars and liquors derived from the process of making bisphenol-A, and there still remains the need to treat the tars and residues resulting from the initial reaction of the phenol and acetone to recover all useful products in order to enhance the value of the bisphenol-A process."

The present invention is an improvement in the utilization of the tar residues of the commercial bisphenol process, using it as a feedstock to prepare phenol and aminophenylhydroxyphenyl alkanes (AHAs).

SUMMARY OF THE INVENTION

The invention comprises a process for the preparation of aminophenylhydroxyphenyl alkanes which comprises;

providing a tarry residue of higher boiling by-products of the condensation of phenol and a ketone obtained by distillation/ evaporation of a mother liquor obtained after separation of bisphenol;

heating the tarry residue with an arylamine salt; and separating the resulting aminophenylhydroxyphenylalkanes.

DETAILED DESCRIPTION OF THE PREFERRED EMBODIMENT OF THE INVENTION

The method of the present invention provides an economical means to recover bisphenol-A and other valuable residues from admixture with contaminant materials resulting from the bisphenol-A preparative process in effluent streams, without employing cracking procedures to convert bisphenol-A back to phenol and acetone.

The commercially important processes for preparing bisphenol-A comprise condensation of 2 moles of phenol with a mole of acetone in the presence of an acid catalyst and a stoichiometric excess of the phenol reactant; see for example the U.S. Pat. Nos. 4,766,254 and 4,847,433 mentioned above.

The reaction zone effluent is conventionally continuously withdrawn and fed to a system for separation of the desired product bisphenol-A. As mentioned earlier, this effluent comprises unreacted phenol, unreacted acetone, acid residues of the catalyst, water and isomers of bisphenol-A in admixture with the desired bisphenol-A. The isomers of interest are position isomers wherein the hydroxy groups are other than in the p-configuration. The effluent may be treated first by cooling to precipitate a crystalline 1:1 adduct of bisphenol-A with phenol, and separating the solid adduct. The remaining mother liquor generally contains appreciable quantities of residual bisphenol-A and valuable isomers thereof. It is this liquor which may provide a starting material for the method of the present invention.

At least a portion of the mother liquor may be treated by heating to a temperature within the range of from about 55° C. to 95° C. to promote isomerization of related isomers to bisphenol-A or recycled through the reaction zone described above for subsequent condensations in the process line.

A portion of the mother liquor may also be treated with ion-exchange resins, filtered, distilled to remove phenol and solvents.

The feedstock employed in the process of the present invention is obtained from a portion of the mother liquor, distilled/evaporated to leave a tarry residue of higher boiling by-products of the acetone-phenol condensation, after separation (usually by crystallization and filtration) of the desired bisphenol-A. In one embodiment, the mother liquor is purged from the bisphenol-A synthesis line and subjected to distillation/evaporation under progressively (sequentially) higher vacuum/temperature conditions in order to separate the stream into four fractions. A first distillation column is operated under vacuum and temperature conditions to remove an overhead fraction containing relatively pure phenol (eg >97% purity). The bottoms of the first column are fed to a second distillation column. This second column operates under reduced pressures and elevated temperature conditions which remove a colored "light" fraction consisting mainly of residual isomers of bisphenol-A and Chroman along with other byproducts with known and unknown chemical structure. This lights fraction can be purged from the plant and discarded, or subjected to additional recovery by this or other processes. The bottoms of the second column are fed to a third column. The overheads of this third column typically contain 60–90% pure bisphenol-A depending on the temperature and pressure conditions used. The bottoms of the third column contain "heavies" or tars which are purged from the process and used as the feedstock in the present invention.

The feedstock provided as described above is, according to the present invention heated with an arylamine acid salt to react with residue bisphenol-A values in the tar feedstock. Advantageously, the arylamine is an acid salt of an arylamine selected from those of the formula:

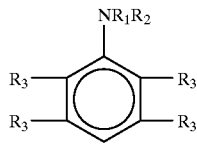

(I)

wherein $R_1$ and $R_2$ are each independently hydrogen or alkyl; and each $R_3$ independently represents hydrogen, halogen, hydrocarbyl or alkoxy.

The term "hydrocarbyl" as used herein means the monovalent moiety obtained upon removal of a hydrogen atom from a parent hydrocarbon. Representative of hydrocarbyl or alkyl of 1 to 25 carbon atoms, inclusive, such as methyl, ethyl, propyl, butyl, pentyl, hexyl, heptyl, octyl, nonyl, undecyl, decyl, dodecyl, octadecyl, nonodecyl, eicosyl, heneicysyl, docosyl, tricosyl, tetracosyl, pentacosyl and the isomeric forms thereof; aryl of 6 to 25 carbon atoms, inclusive, such as a phenyl, tolyl, xylyl, napthyl, biphenyl, tetraphenyl and the like; aralkyl of 7 to 25 carbon atoms, inclusive, such as benzyl, phenethyl, phenpropyl, phenbutyl, phenhexyl, napthoctyl and the like; cycloalkyl of 3 to 8 carbon atoms, inclusive, such as cyclopropyl, cyclobutyl, cyclopentyl, cyclohexyl, cycloheptyl, cyclooctyl and the like; alkenyl of 2 to 25 carbon atoms, inclusive, such as vinyl, allyl, butenyl, pentenyl, hexenyl, octenyl, nonenyl, decenyl, undececyl, dodecenyl, tridecenyl, pentadecenyl, octadecenyl, pentacosynyl and isomeric forms thereof.

The term "alkenylene" means the divalent moiety obtained on removal of two hydrogen atoms, each from a non-adjacent carbon atom of a parent hydrocarbon and includes alkenylene of 3 to 10 carbon atoms, inclusive, such as 1,3-propenylene, 1,4-butenylene, 1,5-pentenylene, 1,8-octenylene, 1,10-decenylene and the like.

The terms "substituted hydrocarbyl", "substituted alkyl", "substituted alkenyl", "substituted alkenylene" and substituted aralkyl" as used herein means the hydrocarbyl moiety as previously defined wherein one or more hydrogen atoms have been replaced with an inert group, i.e.; a chemical group which does not adversely affect the desired catalytic function of the catalyst of formula (III). Representative of such groups are amino-, phosphino-, hydrocarbyl, quaternary nitrogen (ammonium), quaternary phosphorus (phosphonium), hydroxyl-, amide, alkoxy, mercapto-, nitro-, alkyl, halo-, sulfone, sulfoxide, phosphate, phosphite, carboxylate groups and the like.

The term "alkoxy" as used herein means a monovalent moiety of the formula

-O-alkyl wherein alkyl is as defined above.

The term "halogen" is used in its conventional sense embrosive of chlorine, bromine, iodine and fluorine.

The arylamine compounds of the formula (I) given above are generally well known as are methods of that preparation. Representative of the compounds (I) are aniline, 2,-bromoaniline, 2,5-dibromoaniline, 2-methylaniline, 2-ethylaniline, 2,5-diethylaniline, 2-methyoxyaniline, 2,3-dimethoxyaniline, 2-ethoxyaniline, 2,3-diethoxy-aniline and the like.

Preferably the arylamines of formula (I) are employed in the process of the invention as the mineral acid salts thereof, which may be preformed or formed in-situ in the reaction mixture.

Heating the tar feedstock with a proportion of the arylamine (I) may be to a temperature within the range of from about 100° C. to about 200° C. under atmospheric pressures. Advantageously, heating is carried out under an inert atmosphere, such as nitrogen gas atmospheres.

Progress of the reaction may be followed by conventional analytic procedures to observe the disappearance of the arylamine (I) reactant. Upon completion of the desired reaction, the product aminophenylhydroxyphenylpropane may be separated by conventional techniques such as precipitation, crystallization, filtration and like procedures.

The following example and preparations describe the manner and process of making and using the invention and set forth the best mode contemplated by the inventor of carrying out the invention but are not to be construed as limiting the invention.

PREPARATION 1

A bisphenol-A process by-product stream containing approximately 83.3% phenol, 9.8% bisphenol-A, 2.3% 2-(4-hydroxyphenyl)2-(2-hydroxyphenyl) propane (o, p bisphenol-A) and 4.6% other by-products is continually passed through a jacketed "isomerization" reactor containing a bed of sulfonated polystyrene resin (Rhom & Haas Amberlyst 31; 16500 lbs of catalyst-dry basis) at a temperature of 74° C. and a flow of 20 gpm. At least a portion of the reaction effluent (82.5% phenol, 11.8% bisphenol-A, 1.6% 2-(4-hydroxy-phenyl)2-(2-hydroxyphenyl) propane and 4.1% other by-products) is then passed through vessel at a temperature of 72° C. containing 1300 lbs (dry basis) of Rhom & Haas Amberlyst A-21 weakly basic anionic resin to reduce the concentration of acidic species to <2 ppm. Passing the resulting effluent solution through a filter removes particulates larger than 2 microns.

At least a portion of the resulting solution is then fed to a phenol distillation column which operates at a pressure of 30 mm of mercury and a temperature of 218° C. This removes the phenol as an approximately 99% pure colorless overhead material. The bottoms contain about 1% phenol and is continuously fed to a second distillation column which operates at a temperature of 224° C. and approximately 1–2 mm of Hg. The overhead stream from this column consists mainly of bisphenol-A isomers, primarily o, p-bisphenol-A, 2,2,4-trimethyl-4(4-hydroxyphenol) Chroman, bisphenol-A and other by-products. This stream is discarded. The bottoms is fed to a third distillation column which operates at a temperature of 260° C. to 290° C. (500–550° F.) and a pressure of 1–2 mm of Hg. The column overheads consist of circa 80+% pure bisphenol-A which can be recycled back to the bisphenol-A manufacturing process. The bottoms of the last column contain a highly colored tar (<30% bisphenol-A and >70% heavy phenolic process by-products) which is the feedstock for the following example.

In accordance with the present invention, the feedstock is heated to a temperature of from about 100° C. to 200° C. in the presence of a proportion of aniline hydrochloride for a period of time sufficient to form the desired aminophenylhydroxyl-phenylpropane (AHP). Heating is preferably under an inert atmosphere such as nitrogen. Generally, under ambient atmospheric pressures, this occurs within 1 to 2 hours and can be followed by conventional analytical techniques. Phenol is a by-product of the process of the invention and can be stripped from the reaction mixture.

The proportion of aniline hydrochloride added to the tar residue is not critical, and equal weights (w/w) can be reacted together.

Upon completion of the reaction, the AHP can be separated from the reaction mixture by conventional techniques, for example by precipitation at a pH of from 10 to 12 in the presence of base and a following filtration to obtain product yields of 55–65% (95% purity).

EXAMPLE 1

A 250 ml three neck flask equipped with an overhead stirrer, a thermometer, a temperature controller, a condenser, a dean stark trap, a nitrogen inlet and outlet was charged with 68 grams of aniline hydrochloride and 60 grams of BPA Tar from Preparation 1, supra.

Using an oil bath, the charge delineated above was heated to 160° C. The reaction temperature was maintained at 160° C. for two hours along with a flow of nitrogen. Stirring of the reaction mixture was started after the reactants had melted.

After two hours at 160° C., the reaction mixture was allowed to cool to 110° C., followed by the addition of 200 ml of water. At this stage, nitrogen flow was stopped. The pH of the reaction mixture was then adjusted to pH:12 with a solution of sodium hydroxide. During the pH adjustment a precipitate formed and at pH:12 was collected by filtration. The resulting presscake was washed with Toluene (50 ml) and oven-dried. 25 grams of the product was isolated and 10 grams of phenol were collected in the trap.

$^1$H NMR of the product AHP was identical to that of a known AHP sample.

This process provides an efficient, low cost method of recovering phenol and other materials of value from process streams which would be normally disposed of by burning. Although the process of the invention has been described above in reference to the preferred embodiment wherein the process stream or feedstock is the residual tar from a commercial production of bisphenol A, those skilled in the art will appreciate that the spirit and scope of the invention applies to the use and recovery of bisphenol values from tars resulting from processes for condensation of phenols with ketones. Thus, the process of the present invention may be used to recover bisphenols of the formula:

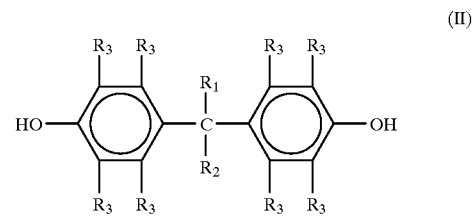
(II)

wherein $R_1$, $R_2$ and $R_3$ are alkyl. These bisphenols (II) generally result from condensation of phenols with ketones according to the schematic formula:

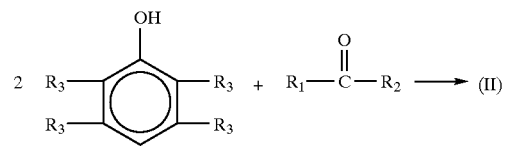

wherein $R_1$, $R_2$, and $R_3$ have the meanings previously ascribed to them.

Preferably the tars employed results from processes for the preparation of bidphenols(II) wherein $R_1$, and $R_2$ are alkyl, aryl, alkaryl, cycloalkyl, cycloalkylaryl, halogen substituted alkyl, or alkoxy; preferably having 1 to 10 carbon atoms and most preferably 1 to 6 carbon atoms. $R_3$ is preferably hydorgen, halogen, alkyl as 1 to 6 carbon atoms, cycloalkyl of 4 to 6 carbon atoms, aryl; most preferably hydrogen, alkyl of 1 to 6 carbon atoms or halogen.

What is claimed is:

1. A process for the preparation of aminophenylhydroxyphenyl alkanes which comprises:
    providing a tarry residue of higher boiling by-products of the condensation of phenol and a ketone obtained by distillation/evaporation of a mother liquor obtained after separation of bisphenol;
    heating the tarry residue with an arylamine salt; and
    separating the resulting aminophenylhydroxyphenyl alkanes.

2. The process of claim 1 wherein heating is to a temperature within the range of from about 100° C. to 200° C. under atmospheric pressures.

3. The process of claim 1 wherein separation is carried out by precipitation at pH of from about 10 to 12.

4. The process of claim 1 wherein the arylamine is of the formula:

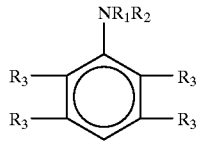
(I)

wherein $R_1$, and $R_2$ are each independently selected from the group consisting of hydrogen and alkyl; each R3 independently represents hydrogen, halogen, hydrocarlyl or alkoxy.

5. The process of claim 4 wherein the arylamine is aniline.

6. The process of claim 1 wherein the phenol is of the formula:

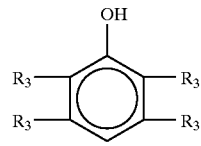

wherein each $R_3$ is independently hydrogen, halogen, hydrocarbyl or alkoxy and the ketone is of the formula:

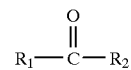

wherein $R_1$ and $R_2$ are each independently alkyl.

* * * * *